US00PP36851P2

(12) United States Plant Patent
van Sambeek

(10) Patent No.: US PP36,851 P2
(45) Date of Patent: Jul. 22, 2025

(54) ***PHLOX* PLANT NAMED 'Dophlolawhi'**

(50) Latin Name: *Phlox subulata*
Varietal Denomination: Dophlolawhi

(71) Applicant: DUMMEN GROUP B.V., De Lier (NL)

(72) Inventor: Ellen van Sambeek, Oegstgeest (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 18/810,408

(22) Filed: Aug. 20, 2024

(51) Int. Cl.
*A01H 5/02* (2018.01)
*A01H 6/70* (2018.01)

(52) U.S. Cl.
USPC ..... Plt./320

(58) Field of Classification Search
USPC ..... Plt./320
See application file for complete search history.

(56) References Cited

U.S. PATENT DOCUMENTS

PP13,420 P3 * 12/2002 Cammarota ..... A01H 6/70
Plt./320

* cited by examiner

*Primary Examiner* — Susan McCormick Ewoldt
(74) *Attorney, Agent, or Firm* — C. Anne Whealy

(57) ABSTRACT

A new and distinct cultivar of *Phlox* plant named 'Dophlolawhi', characterized by its outwardly spreading to creeping and mounding plant habit; moderately vigorous growth habit; dark green-colored leaves; freely flowering habit; relatively late flowering; white-colored flowers; and good garden performance.

1 Drawing Sheet

Botanical designation: *Phlox subulata.*
Cultivar denomination: 'DOPHLOLAWHI'.

CROSS-REFERENCED TO CLOSELY-RELATED APPLICATIONS

A European Community Plant Breeder's Rights application for the instant plant was filed by the Applicant/Assignee, Dümmen Group B.V. of De Lier, The Netherlands on Jun. 17, 2024, application number 2024/1414. Foreign priority is not claimed to this application.

BACKGROUND OF THE INVENTION

The present invention relates to a new and distinct cultivar of *Phlox*plant, botanically known as *Phlox subulata,* commonly called Creeping or Moss *Phlox* and hereinafter referred to by the name 'Dophlolawhi'.

The new *Phlox* plant is a product of a planned breeding program conducted by the Inventor in Aalsmeer, The Netherlands. The objective of the breeding program was to create new freely-flowering Creeping *Phlox* plants with attractive flowers.

The new *Phlox* plant originated from a cross-pollination made by the Inventor in April 2013 in Aalsmeer, The Netherlands, of a proprietary selection of *Phlox subulata* identified as code number SB10-000020-005,not patented, as the female, or seed, parent with a proprietary selection of *Phlox subulata* identified as code number SB10-000002-006, not patented, as the male, or pollen, parent. The new *Phlox* plant was discovered and selected by the Inventor as a single flowering plant from within the progeny of the stated cross-pollination in a controlled environment in Aalsmeer, The Netherlands in April 2014.

Asexual reproduction of the new *Phlox* plant by vegetative cuttings in a controlled environment in Aalsmeer, The Netherlands since June 2014 has shown that the unique features of this new *Phlox* plant are stable and reproduced true to type in successive generations.

SUMMARY OF THE INVENTION

Plants of the new *Phlox* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dophlolawhi'. These characteristics in combination distinguish 'Dophlolawhi' as a new and distinct *Phlox* plant:

1. Outwardly spreading to creeping and mounding plant habit.
2. Moderately vigorous growth habit.
3. Dark green-colored leaves.
4. Freely flowering habit.
5. Relatively late flowering.
6. White-colored flowers.
7. Good garden performance.

Plants of the new *Phlox* differ primarily from plants of the female parent selection in flower color as plants of the new *Phlox* have white-colored flowers whereas plants of the female parent selection have pink-colored flowers.

Plants of the new *Phlox* differ primarily from plants of the male parent selection in flowering time as plants of the new *Phlox* flower later in the spring than plants of the male parent selection.

Plants of the new *Phlox* can also be compared to plants of *Phlox subulata* 'Crimson Beauty', not patented. In side-by-side comparisons, plants of the new *Phlox* and 'Crimson Beauty' differ in the following characteristics:

1. Plants of the new *Phlox* flower later than plants of 'Crimson Beauty'.
2. Plants of the new *Phlox* and 'Crimson Beauty' differ in flower color as plants of the new *Phlox* have white-colored flowers whereas plants of 'Crimson Beauty' have bright rosy red-colored flowers.

BRIEF DESCRIPTION OF THE PHOTOGRAPH

The accompanying colored photograph illustrates the overall appearance of the new *Phlox* plant showing the colors as true as it is reasonably possible to obtain in colored reproductions of this type. Colors in the photograph may differ slightly from the color values cited in the detailed botanical description which accurately describe the colors of the new *Phlox* plant.

The photograph is a side perspective view of typical flowering plant of 'Dophlolawhi' grown in a container.

DETAILED BOTANICAL DESCRIPTION

The aforementioned photograph and following observations, measurements and values describe plants grown during the late spring in containers in an outdoor nursery in Puerto Lumbreras, Spain under cultural practices typical of commercial *Phlox* production. Plants were pinched one time two weeks after planting rooted young plants and plants were 46 weeks old when the photograph and the description were taken. In the following description, color references are made to The Royal Horticultural Society Colour Chart, Fifth Edition, except where general terms of ordinary dictionary significance are used.

Botanical classification: *Phlox subulata* 'Dophlolawhi'.

Parentage:

*Female, or seed, parent*.—Proprietary selection of *Phlox subulata*identified as code number SB10-000020-005, not patented.

*Male, or pollen, parent*.—Proprietary selection of *Phlox subulata*identified as code number SB10-000002-006, not patented.

Propagation:

*Type*.—By vegetative cuttings.

*Time to initiate roots, summer*.—About 16 days at temperatures about 26° C.

*Time to initiate roots, winter*.—About three weeks at temperatures about 23° C.

*Time to produce a rooted young plant, summer*.—About 24 days at temperatures about 23° C.

*Time to produce a rooted young plant, winter*.—About four weeks at temperatures about 18° C.

*Root description*.—Medium in thickness, fibrous; typically white to light yellow in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Herbaceous perennial typically grown as a container and garden plant; outwardly spreading to creeping and mounding plant habit; moderately vigorous growth habit and slow growth rate.

*Plant height*.—About 21 cm.

*Plant width* (*spread*).—About 21 cm.

*Lateral branches*.—Branching habit: Freely branching habit with about seven primary lateral branches each with about five secondary lateral branches developing per plant; pinching enhances branching potential. Length: About 19 cm. Diameter: About 3 mm. Internode length: About 2 cm. Strength: Strong. Aspect: Erect to about 90° from vertical. Texture and luster: Pubescent; glossy. Color, developing: Close to 144C. Color, developed: Close to 152D.

Leaf description:

*Arrangement*.—Opposite, decussate; simple; sessile.

*Length*.—About 2 cm.

*Width*.—About 3 mm.

*Shape*.—Lanceolate, subulate.

*Apex*.—Acuminate.

*Base*.—Cuneate.

*Margin*.—Entire.

*Texture and luster, upper and lower surface*.—Smooth, glabrous; glossy.

*Venation pattern*.—Hyphodromous, only midvein discernible.

*Color*.—Developing leaves, upper surface: Close to 137A. Developing leaves, lower surface: Close to 137D. Fully expanded leaves, upper surface: Close to N137A; venation, close to N137A. Fully expanded leaves, lower surface: Close to 137B; venation, close to 137B.

Flower description:

*Flower type and flowering habit*.—Single rotate and salverform flowers arranged in terminal and lateral panicles; flowers face mostly upright to outwardly depending on position on inflorescence; freely flowering habit with about five open flowers per inflorescence and about 280 flowers developing per plant during the flowering season.

*Fragrance*.—Fragrant, sweet and pleasant.

*Natural flowering season*.—Plants begin flowering about 46 weeks after planting; plants flower for about three to four weeks during the late spring in the garden in Spain; flowers not persistent.

*Flower buds*.—Height: About 1.6 cm. Diameter: About 5 mm. Shape: Elliptic. Texture and luster: Smooth, glabrous; semi-glossy. Color: Close to NN155D.

*Inflorescence height*.—About 5 cm.

*Inflorescence diameter*.—About 5 cm.

*Flower diameter*.—About 1.8 cm by 1.9 cm.

*Flower depth*.—About 1.3 cm.

*Flower throat diameter*.—About 2 mm.

*Flower tube length*.—About 1.1 cm.

*Flower throat diameter*.—About 2 mm.

*Petals*.—Quantity per flower: Typically five in a single whorl; petals fused at the base into a narrow tube. Lobe length: About 9 mm. Lobe width: About 7 mm. Lobe shape: Obcordate. Lobe apex: Emarginate. Lobe margin: Entire; slightly undulate. Lobe texture and luster, upper and lower surfaces: Smooth, glabrous; matte. Throat texture and luster: Smooth, glabrous; matte. Tube texture and luster: Smooth, glabrous; matte. Color: When opening and fully opened, upper surface: Close to NN155D; venation, close to NN155D; color does not change with subsequent development. When opening and fully opened, lower surface: Close to NN155D; venation, close to NN155D; color does not change with subsequent development. Throat: Close to NN155D; venation, close to NN155D. Tube: Close to NN155A; venation, close to NN155A.

*Sepals*.—Quantity per flower: Typically five in a single whorl, fused towards the base; calyx, tubular in shape. Length: About 9 mm. Width: About 1 mm. Shape: Narrowly deltoid, subulate. Apex: Acuminate. Margin: Entire. Texture and luster, upper surface: Pubescent; glossy. Texture and luster, lower surface: Smooth, glabrous; glossy. Color: When opening and fully opened, upper surface: Close to 143B. When opening and fully opened, lower surface: Close to 143B.

*Peduncles*.—Length: About 9 mm. Diameter: About 2 mm. Strength: Low. Aspect: About 30° from lateral branch axis. Texture and luster: Pubescent; glossy. Color: Close to 145A.

*Pedicels*.—Length: About 3 mm. Diameter: About 1 mm. Strength: Low. Aspect: About 5° from peduncle axis. Texture and luster: Pubescent; glossy. Color: Close to 145A.

*Reproductive organs*.—Stamens: Quantity per flower: Typically five. Filament length: About 4 mm. Filament color: Close to 145D. Anther size: About 0.5 mm by 1 mm. Anther shape: Elliptic. Anther color: Close to 17A. Pollen amount: Abundant. Pollen color: Close to 17A. Pistils: Quantity per flower: One. Pistil length: About 8 mm. Stigma diameter: About 1 mm. Stigma shape: Cleft, three-parted. Stigma color: Close to N144B. Style length: About 5 mm. Style color: Close to 145A. Ovary color: Close to 143A.

*Seeds and fruits*.—To date, seed and fruit development have not been observed on plants of the new *Phlox*.

Garden performance: Plants of the new *Phlox* have been observed to have good garden performance and to tolerate rain, wind, temperatures ranging from about −35° C. to about 35° C. and to be suitable for USDA Hardiness Zones 3 to 9.

Pathogen & pest resistance: To date, plants of the new *Phlox* have not been observed to be resistant to pathogens and pests common to *Phlox* plants.

It is claimed:

1. A new and distinct *Phlox* plant named 'Dophlolawhi' as herein illustrated and described.

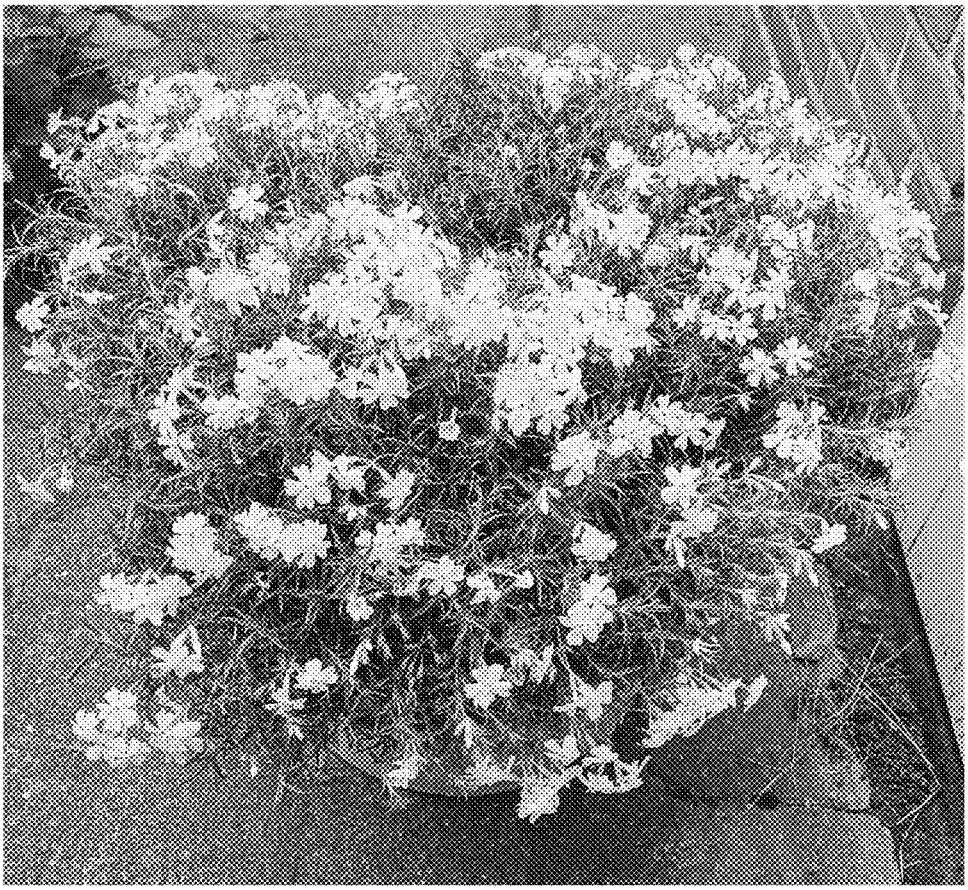

* * * * *